(12) United States Patent
Kooyers

(10) Patent No.: US 10,307,563 B1
(45) Date of Patent: Jun. 4, 2019

(54) SLEEP ENHANCEMENT DEVICE

(71) Applicant: Dustin Kooyers, Grandville, MI (US)

(72) Inventor: Dustin Kooyers, Grandville, MI (US)

(*) Notice: Subject to any disclaimer, the term of this patent is extended or adjusted under 35 U.S.C. 154(b) by 125 days.

(21) Appl. No.: 15/191,722

(22) Filed: Jun. 24, 2016

Related U.S. Application Data

(63) Continuation-in-part of application No. 15/089,950, filed on Apr. 4, 2016, now abandoned, which is a continuation-in-part of application No. 14/943,464, filed on Nov. 17, 2015, now abandoned.

(60) Provisional application No. 62/080,639, filed on Nov. 17, 2014.

(51) Int. Cl.
*A61M 21/02* (2006.01)
*A61M 21/00* (2006.01)

(52) U.S. Cl.
CPC ....... *A61M 21/02* (2013.01); *A61M 2021/005* (2013.01); *A61M 2021/0016* (2013.01); *A61M 2021/0027* (2013.01); *A61M 2021/0044* (2013.01); *A61M 2205/3584* (2013.01); *A61M 2205/505* (2013.01); *A61M 2205/8206* (2013.01); *A61M 2205/8268* (2013.01)

(58) Field of Classification Search
CPC .. A61M 2021/0027; A61M 2021/0044; A61M 21/00; A61M 21/02
See application file for complete search history.

(56) References Cited

U.S. PATENT DOCUMENTS

| | | | |
|---|---|---|---|
| 4,363,181 A | 12/1982 | Hyman et al. | |
| 4,516,950 A | 5/1985 | Berman et al. | |
| 4,568,303 A | 2/1986 | Brown | |
| 4,640,034 A | 2/1987 | Zisholtz | |
| 5,307,051 A | 4/1994 | Sedlmayr | |
| 5,464,381 A | 11/1995 | Wilson | |
| 5,791,775 A | 8/1998 | Douglass, II | |
| 6,084,527 A | 7/2000 | Spector | |
| 6,227,931 B1 | 5/2001 | Shackelford | |
| 6,702,767 B1 * | 3/2004 | Douglas | A61M 21/0094 600/21 |
| 7,346,949 B2 | 3/2008 | Kamrin-Balfour | |
| 2002/0094748 A1 | 7/2002 | Baik | |
| 2008/0125620 A1 * | 5/2008 | McNew | A61M 21/02 600/27 |
| 2012/0100776 A1 | 4/2012 | Jackson et al. | |

* cited by examiner

*Primary Examiner* — Christine H Matthews
(74) *Attorney, Agent, or Firm* — King & Partners, PLC

(57) ABSTRACT

A sleep enhancement device for toddlers and young children, including: a containment assembly and an electronics assembly, wherein both assemblies cooperatively create the psychological appearance that the device is at least one of catching and destroying monsters and/or bad dreams, and provides a soothing, relaxing, deep, and/or healthy sleep.

1 Claim, 4 Drawing Sheets

US 10,307,563 B1

SLEEP ENHANCEMENT DEVICE

CROSS-REFERENCE TO RELATED APPLICATIONS

This application is a continuation-in-part of U.S. application Ser. No. 15/089,950, filed Apr. 4, 2016, entitled "Sleep Enhancement Device" which is a continuation-in-part of U.S. application Ser. No. 14/943,464, filed Nov. 17, 2015, entitled "Children's Sleep Enhancement Device" which claims the benefit of U.S. Provisional Application Ser. No. 62/080,639, filed Nov. 17, 2014, entitled "Children's Sleep Enhancement Device," all of which are hereby incorporated herein by reference in their entirety including all references and appendices cited therein.

BACKGROUND OF THE INVENTION

1. Field of the Invention

The present invention relates in general to a sleep enhancement device for toddlers and young children, and, more particularly, to a novelty consumer product that is intended to be used as a device to help toddlers and young children relax at bedtime by addressing the inherent fear children have for monsters and bad dreams so they can achieve better sleep. The present invention creates the psychological appearance that the device is catching and destroying monsters and bad dreams, and/or enabling them to believe that the device allows them to have positive dreams of their choosing, so a child may have soothing, relaxing, deep, and/or healthy sleep.

2. Background Art

Sleep enhancement devices and novelty toys for toddlers and young children have been known in the art for years and are the subject of a plurality of patents and/or publications, including: U.S. Pat. No. 7,346,949 entitled "Infant Soothing and Sleep Aid," U.S. Pat. No. 6,227,931 entitled "Electronic Interactive Play Environment for Toy Characters," U.S. Pat. No. 6,084,527 entitled "Combined Monitor and Light Box Assembly," U.S. Pat. No. 5,791,775 entitled "Illuminating Mobile," U.S. Pat. No. 5,464,381 entitled "Infant Soothing Seat," U.S. Pat. No. 5,307,051 entitled "Night Light Apparatus and Method for Altering the Environment of a Room," U.S. Pat. No. 4,640,034 entitled "Mobile for Infants," U.S. Pat. No. 4,568,303 entitled "Toy for Electronically Playing Rhythmical Melody upon Rotation or Revolution Thereof," U.S. Pat. No. 4,516,950 entitled "Speaking Toy Employing Chordic Input," U.S. Pat. No. 4,363,181 entitled "Electronic Musical Mobile," United States Patent Application Publication Number 2012/0100776 entitled "Children's Entertainment Device," and United States Patent Application Publication Number 2002/0094748 entitled "Baby Mobile," all of which are hereby incorporated herein by reference in their entirety including all references cited therein.

U.S. Pat. No. 7,346,949 appears to disclose an infant soothing and sleep aid that includes a fabric mat. A pair of removable and adjustable barriers are provided, one on either side, that act as a cradling mechanism to make the infant feel safe and secure in the large crib. The barriers include a soothing device such as a vibration mechanism and white noise mechanism in order to soothe the baby in the form of restricted movement, pleasing sounds, and motion.

U.S. Pat. No. 6,227,931 appears to disclose a child's electronic playset that defines a setting or character environment for various toy characters, play pieces, representing persons or fantasy characters, which the player may move about that environment. Through its electronics the environment possesses built-in intelligence and defines virtual beings through spoken messages which are attributed by the player to the toy characters, creating a virtual universe. Markers identify each toy character to the environment when checked by the environment's sensors enabling the environment to know which characters are present and to call up an appropriate dialog there between to broadcast through a loudspeaker. The environment also keeps track of the time of day, enabling it to know the order in which toy characters are placed in the environment and possess the ability to call up a dialog appropriate to certain hours in the day.

U.S. Pat. No. 6,084,527 appears to disclose a combined monitor and light box assembly that is installable in a crib enclosure occupied by an infant. The assembly which is interactive with the infant includes a light box on whose front face is mounted to a semi-reflective mirror behind which is a film transparency having a photographic image of the infant's mother. When a light bulb in the box is energized to illuminate the transparency, the image of the mother becomes visible to the infant through the mirror which is then effectively transparent. Associated with the light box is a sound-activated switching device connected between the bulb and a power source. The switching device, when activated by crying sounds emanating from the infant, remains activated for a predetermined period to energize the bulb and illuminate the transparency. Also associated with the light box is a record playback unit having stored therein a voice message recorded by the mother addressed to her infant, the unit being rendered operative only when the bulb is energized. Hence when the infant cries, it is then presented with an image of its mother and hears her comforting message, as a consequence of which the infant is induced to stop crying. The monitor which is operative only after the switch is activated, radio-transmits the crying sounds then emanating from the infant to a receiver that can be heard by the mother.

U.S. Pat. No. 5,791,775 appears to disclose a decorative illuminating mobile apparatus including a support member that has an engaging surface that fits a generally flat adjacent anchoring surface such as a ceiling, floor, wall or the like. A first swivel member extends away from the support member. A plurality of separately rotatable appendages are connected sequentially together by a series of additional swivel members that space each appendage apart from another adjacent appendage and away from the support member engaging surface. This arrangement stacks the rotatable appendages vertically so there is a highest appendage and a lowest appendage with a plurality of appendages therebetween for example. At least some of the appendages include a light source that is powered by electricity. An electrical supply is provided for illuminating each light source. The electrical supply includes a rotational light electrical supply connection at the swivels. At least a plurality of the appendages have two rotational connections that are spaced apart along the length of the appendage to ensure a non-coaxial rotation of each appendage relative to its adjacent appendages.

U.S. Pat. No. 5,464,381 appears to disclose a new and improved infant soothing seat comprised of a sound and motion mechanism having a control panel thereon. The control panel consists of a motion control and a sound control. The control panel contains a battery box therein. The battery box houses four batteries therein representing the power source. The sound and motion mechanism has an internal motion control and an internal sound control. The internal motion control consists of a power switch, a speed control, and a variable speed motor. The power switch couples with the power source and the speed control. The speed control couples with the variable speed motor. The variable motor has an eccentric thereattached. The eccentric functions to provide motion for the seat. The internal sound control consists of a power switch, a volume and tone control, and a speaker. The power switch couples with the volume and tone control and the power source. The volume and tone control couples with the speaker.

U.S. Pat. No. 5,307,051 appears to disclose a night light apparatus and method that alters the environment of a room, particularly a darkened room, in response to an audio input such as a child's voice. The apparatus and method is adapted to provide a sense of security to a child in a room in order to improve the child's sleeping habits and reduce or eliminate the child's fear of the dark or the child's fear of being left alone. A predetermined audio level in the darkened room is sensed. If the audio level exceeds a background noise level, a signal is generated and an audio output and a light output are activated. The audio output may include a bedtime story or a soothing song. The light output may include an image such as a cartoon character that is lit. A fire and smoke detector may also be included to activate audio instructions to a child in the event of a fire. The apparatus may be suitably programmed to transmit a signal to a remote location and activate an object warning device and/or a motion generating device.

U.S. Pat. No. 4,640,034 appears to disclose a sound reproducing mobile for connection to cribs or other structures holding an infant. The mobile includes a housing which is releasably secured an audio cassette player. The housing includes clamp means for releasably securing the mobile to the structure holding the infant. The cassette player, when operated, reproduces comforting voices via a loudspeaker and at the same time provides electrical power to a motor for causing the movement of overhanging decorative mobile elements. A voice actuated switch is provided to operate the player and mobile in automatic response to the detection of ambient sound. The player can also be operated manually. The cassette player is releasably secured to the mobile so that it can be removed for independent use thereof.

U.S. Pat. No. 4,568,303 appears to disclose a tune playing rotary toy that comprises a centrifugally-actuated tune player comprising a casing having a centrifugally-operable switch, a music synthesizer, and an energy cell. Upon rotation of the toy, it will experience centrifugal force, which will close the switch, which will in turn apply electrical energy from the cell to the circuit so that the stored tune will be emitted during rotation. The tune player may be mounted within or upon a toy gyroscopic top, (e.g., of the stringless type), or it may be self-contained with a spinner point and a manual spinning portion. The self-contained version may also be covered with sponge rubber and attached to a twirling string for swinging in a wide arc, preferably by means of a handle on the end of the string opposite the tune player. The centrifugally-operable switch comprises a movable contact comprising a weight suspended at the end of a cantilever rod and an L-, U-, or O-shaped fixed contact for sensing motion of the movable contact in any of a variety of directions.

U.S. Pat. No. 4,516,950 appears to disclose a toy including an apparatus for producing a desired sequence of sounds and chordic keyboard apparatus for operating same. The desired sequence of sounds may be human speech, music or any other desired sequence of sounds. In a preferred embodiment of the invention a talking doll is provided.

U.S. Pat. No. 4,363,181 appears to disclose a mobile that is rotated by an energy storage device to which energy is periodically transferred by a motor which is in turn controlled by an electronic circuit. The electronic circuit simultaneously controls a loudspeaker to produce a wide variety of music with variations in tune, tonal quality, key, tempo, and loudness.

United States Patent Application Publication Number 2012/0100776 appears to disclose a children's entertainment device having a stepper motor drive system that is configured to drive a rotatable entertaining element. In certain embodiments, the stepper motor is configured to rotate a drive shaft operatively connected to a damper, which is configured to damp the intermittent rotational motion output by the stepper motor in order to smoothly and continuously rotate an entertaining element, such as in a children's mobile.

United States Patent Application Publication Number 2002/0094748 appears to disclose a device with multiple functions that provides fascinating and engaging entertainment in addition to intellectual stimulation for an infant or child. It provides stimulation and fun at the same time.

While the above-identified patents and/or publications do appear to disclose various sleep enhancement devices and novelty products for toddlers and young children, their configurations remain non-desirous and/or problematic inasmuch as, among other things, none of the above-identified sleep enhancement devices and novelty products appear to be configured to provide the psychological appearance that the sleep enhancement devices and/or novelty toys are catching and/or destroying monsters and bad dreams, and/or enabling them to believe that the device allows them to have positive dreams of their choosing, so a child may have a soothing, relaxing, deep, and/or healthy sleep.

These and other objects of the present invention will become apparent in light of the present specification, claims, and appended drawings.

BRIEF DESCRIPTION OF THE DRAWINGS

Certain embodiments of the present invention are illustrated by the accompanying figures. It will be understood that the figures are not necessarily to scale and that details not necessary for an understanding of the invention or that render other details difficult to perceive may be omitted. It will be further understood that the invention is not necessarily limited to the particular embodiments illustrated herein.

The invention will now be described with reference to the drawings wherein.

SUMMARY OF THE INVENTION

Figure 1:
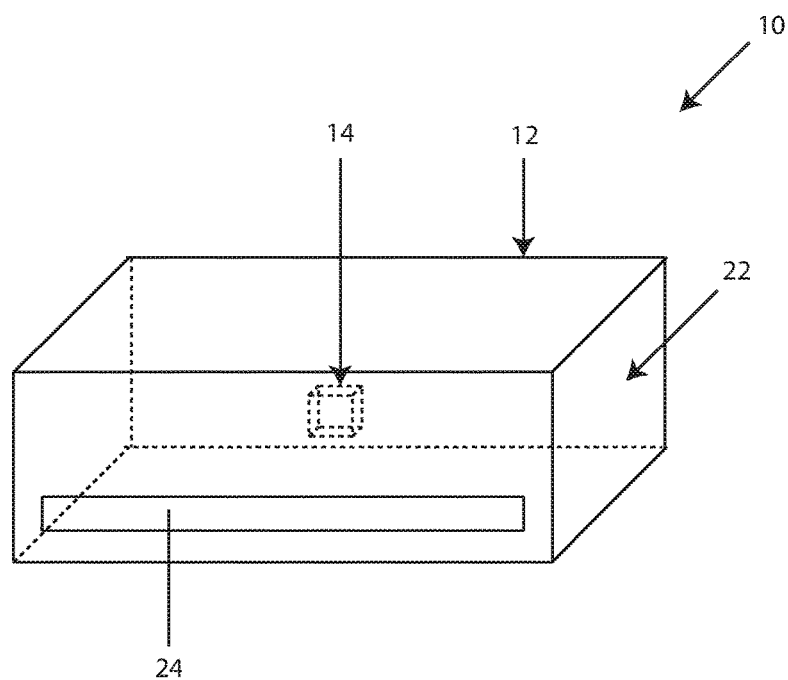
FIG. 1 of the drawings is a perspective view of a sleep enhancement device, in accordance with the present invention, showing a containment assembly and a representation of an electronics assembly.

The present invention is directed to, in one embodiment, a sleep enhancement device for toddlers and young children, comprising, consisting essentially of, and/or consisting of: (a) a containment assembly, wherein the containment assembly comprises: (1) at least one sidewall having an inner surface and an outer surface, (2) a top wall having an inner surface and an outer surface, (3) a bottom wall having an inner surface and an outer surface, (4) wherein at least one of the at least one sidewall, the top wall, and the bottom wall comprises an aperture and (5) wherein the at least one sidewall, the top wall, and the bottom wall are in a spaced-apart relationship to define an internal chamber therebetween; (b) means for creating the psychological appearance that the device is at least one of catching and destroying monsters and/or bad dreams; and (c) means for providing a soothing, relaxing, deep, and/or healthy sleep.

The present invention is also directed to a sleep enhancement device, adapted to create the psychological appearance that the device is catching and destroying monsters and bad dreams, so that a child may have soothing, relaxing, deep, and/or healthy sleep, comprising; (a) a containment assembly, wherein the containment assembly comprises: (1) at least one sidewall having an inner surface and an outer surface, wherein the at least one sidewall comprises an aperture; (2) a top wall having an inner surface and an outer surface, (3) a bottom wall having an inner surface and an outer surface, and (4) wherein the at least one sidewall, the top wall, and the bottom wall are in a spaced-apart relationship to define an internal chamber therebetween; and (b) an electronics assembly, wherein the electronics assembly comprises an energy source, a light source, a primary user interface, a circuit board, and a speaker; (1) wherein the energy source is at least partially contained within the internal chamber of the containment assembly, and wherein the energy source is in electrical communication with at least one of the circuit board, and the light source; (2) wherein the circuit board is at least partially contained within the internal chamber of the containment assembly, and wherein the circuit board is in electrical communication with at least one of the energy source, the light source, the primary user interface, and the speaker; (3) wherein the primary user interface is associated with at least one of the at least one sidewall, the top wall, and the bottom wall of the containment assembly, and wherein the primary user interface is in electrical communication with the circuit board; (4) wherein the light source is at least partially contained within the internal chamber of the containment assembly, and wherein the light source is in electrical communication with at least one of the energy source, and the circuit board; and (5) wherein the speaker is at least partially contained within the internal chamber of the containment assembly, and wherein the speaker is in electrical communication with the circuit board.

In a preferred embodiment of the present invention, the at least one sidewall of the containment assembly comprises a front sidewall, a rear sidewall, a left sidewall, and a right sidewall.

In another preferred embodiment of the present invention, the containment assembly comprises the general geometry of a cube, a cuboid, a tetrahedron, a pyramid, a square pyramid, a hexagonal pyramid, a prism, a triangular prism, a pentagonal prism, a hexagonal prism, an octahedron, a dodecahedron, an icosahedron, a cylinder, a cone, a sphere, and/or an ellipsoid.

In yet another preferred embodiment of the present invention, the energy source of the electronics assembly comprises an AC power supply, a DC power supply, an AC-DC power supply, a primary electrochemical cell, a secondary electrochemical cell, and/or a fuel cell.

In a preferred embodiment of the present invention, the circuit board of the electronics assembly comprises one or more of a battery, a bridge rectifier, a capacitor, a central processing unit, a communications port, a control board, a crystal, a diode, a fuse, a graphics board, an inductor, an input port, an integrated circuit, a microprocessor, a memory module, an oscillator, an output port a potentiometer, a receiver, a relay, a resistor, a semiconductor, a transformer, a transistor, a tuner, a video processing unit, a wired communications hub, and/or a wireless communications hub.

In another preferred embodiment of the present invention, the light source of the electronics assembly comprises one or more of a light-emitting diode, an organic light-emitting diode, a tri-color (RGB) light-emitting diode, an incandescent bulb, a tungsten-halogen bulb, a xenon bulb, a fluorescent bulb, a compact fluorescent lamp, a high-intensity discharge bulb and/or an electroconductive, lightable paint and/or material.

In yet another preferred embodiment of the present invention, the primary user interface of the electronics assembly comprises a graphical user interface and/or a circuit board having a plurality of user interface buttons.

In another aspect of the present invention, the speaker of the electronics assembly comprises a mini-speaker and/or a micro-speaker.

In a preferred embodiment of the present invention, the electronics assembly further comprises a switch. The switch is preferably associated with one or more of the at least one sidewall, the top wall, and/or the bottom wall of the containment assembly. The switch is also preferably in electrical communication with the energy source and/or the light source.

In another preferred embodiment of the present invention, the electronics assembly further comprises a microphone that is preferably in electrical communication with the circuit board.

In yet another preferred embodiment of the present invention, the containment assembly further comprises a reservoir, container, or other method for containing a scented product, and wherein the electronics assembly further comprises a fan. The fan is preferably in electrical communication with the circuit board and adapted to displace the scented product away from the sleep enhancement device and into the room of a user.

In accordance with the present invention, the electronics assembly preferably further comprises a thermo sensor that is in electrical communication with the circuit board.

In a preferred embodiment of the present invention, the electronics assembly further comprises a display that is in electrical communication with the circuit board, and adapted to display one or more of alpha-numeric content, temperature, time, image and/or graphic.

In another preferred embodiment of the present invention, the electronics assembly further comprises an image sensor that is in electrical communication with the circuit board.

Additionally, the electronics assembly preferably further comprises one or more of a secondary energy source, a secondary light source, a secondary user interface, a secondary circuit board, a secondary speaker, a vibration mechanism, and/or a white noise generator.

In a preferred embodiment of the present invention, the electronics assembly further comprises a tactile sensor that is in electrical communication with the circuit board.

DETAILED DESCRIPTION OF THE INVENTION

While this invention is susceptible of embodiment in many different forms, there is shown in the drawings and will be described herein in detail, one or more specific embodiments with the understanding that the present disclosure is to be considered as an exemplification of the principles of the invention and is not intended to limit the invention to the embodiments illustrated.

It will be understood that like or analogous elements and/or components, referred to herein, may be identified throughout the drawings by like reference characters. In addition, it will be understood that the drawings are merely schematic representations of one or more embodiments of the invention, and some of the components may have been distorted from their actual scale for purposes of pictorial clarity.

Figure 2:
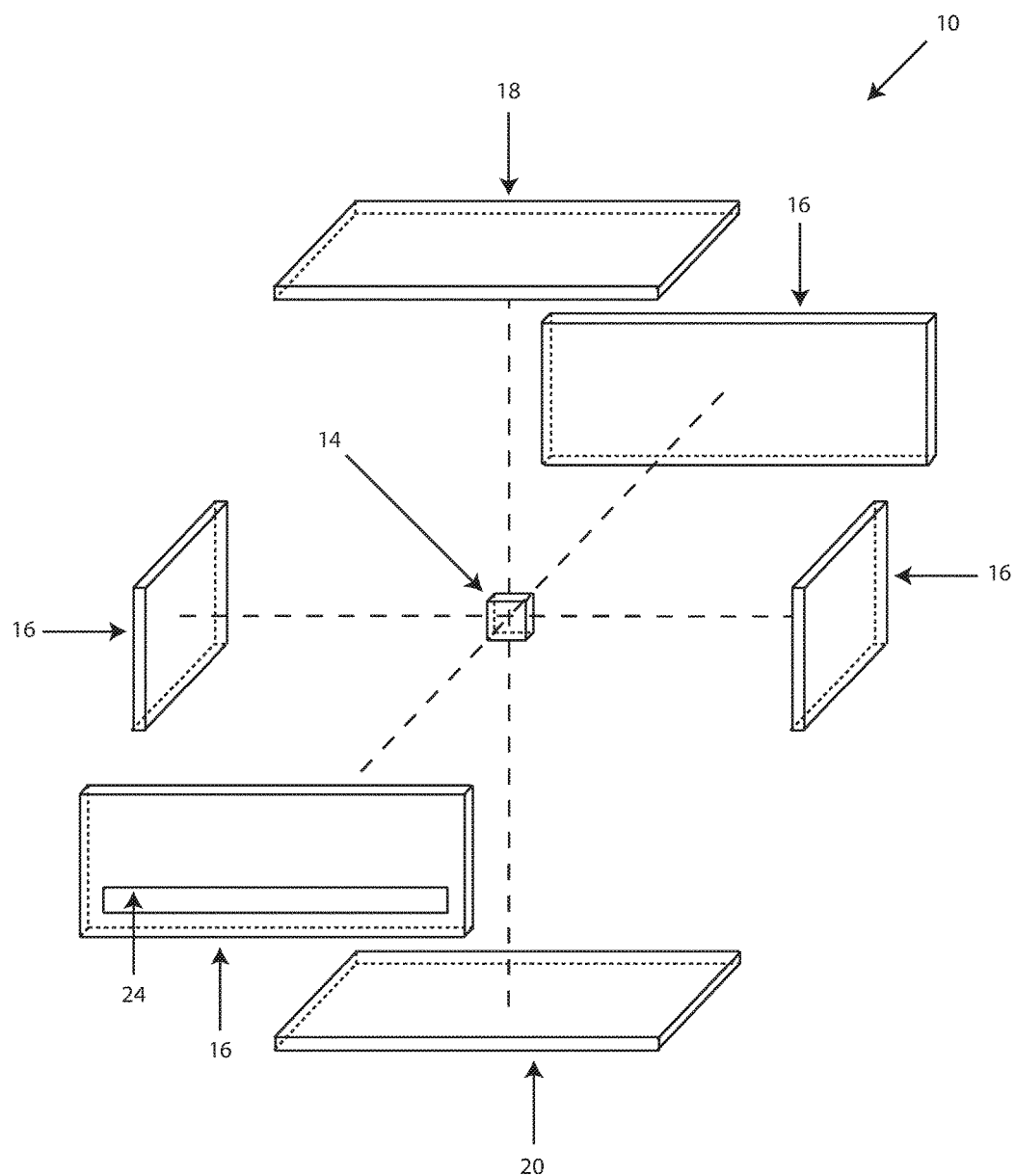
FIG. 2 of the drawings is an exploded perspective view of a sleep enhancement device, in accordance with the present invention, showing a containment assembly and a representation of an electronics assembly.
Figure 3:
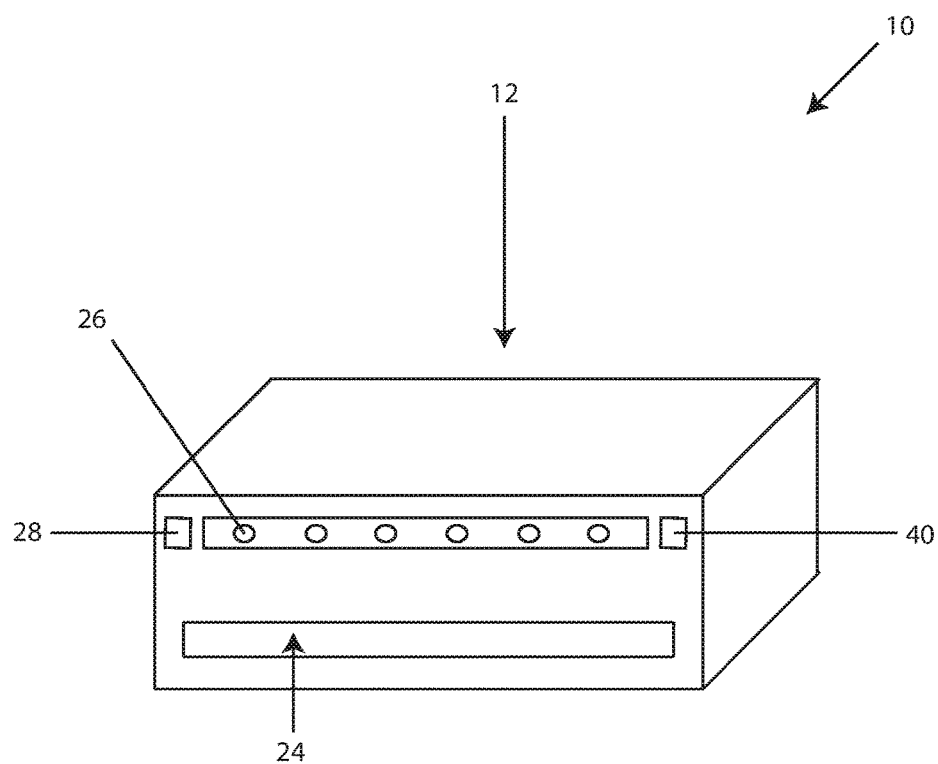
FIG. 3 of the drawings is a perspective view of a sleep enhancement device fabricated in accordance with the present invention.

Referring now to the drawings, and to FIGS. 1-3 in particular, sleep enhancement device 10 is shown as generally comprising containment assembly 12 and electronics assembly 14. Sleep enhancement device 10 is preferably suitable for toddlers and young children who have bad dreams and/or are otherwise afraid to sleep alone—typically at night. Containment assembly 12 and electronics assembly 14 of sleep enhancement device 10 cooperatively create the psychological appearance that the device is at least one of catching and destroying monsters and/or bad dreams by, for example, audio and/or visual output. Such output provides a soothing, relaxing, and deep, healthy sleep to an otherwise anxious and/or afraid toddler and/or young child. Sleep enhancement device 10 also provides better sleep for the parents and/or caregiver because they are able to have uninterrupted rest.

Containment assembly 12 preferably comprises one or more sidewalls 16 having inner surfaces and outer surfaces, top wall 18 having an inner surface and an outer surface, and bottom wall 20 having an inner surface and an outer surface. Sidewalls 16, top wall 18 and bottom wall 20 are preferably spaced-apart from each other to define an internal chamber 22 therebetween. Aperture 24 is preferably associated with one or more of sidewalls 16. Aperture 24, in cooperation with certain components of electronic assembly 14 (e.g., light source, speaker, etcetera) provides the toddler or young child with the psychological appearance that the device is at least one of catching and destroying monsters and/or providing a soothing environment for the child.

Referring now to FIG. 2, containment assembly 12 preferably includes a front sidewall, a rear sidewall, a left sidewall, and a right sidewall.

In accordance with the present invention, containment assembly 12 preferably comprises the general geometry of a cube, a cuboid, a tetrahedron, a pyramid, a square pyramid, a hexagonal pyramid, a prism, a triangular prism, a pentagonal prism, a hexagonal prism, an octahedron, a dodecahedron, an icosahedron, a cylinder, a cone, a sphere, and/or an ellipsoid.

Figure 4:
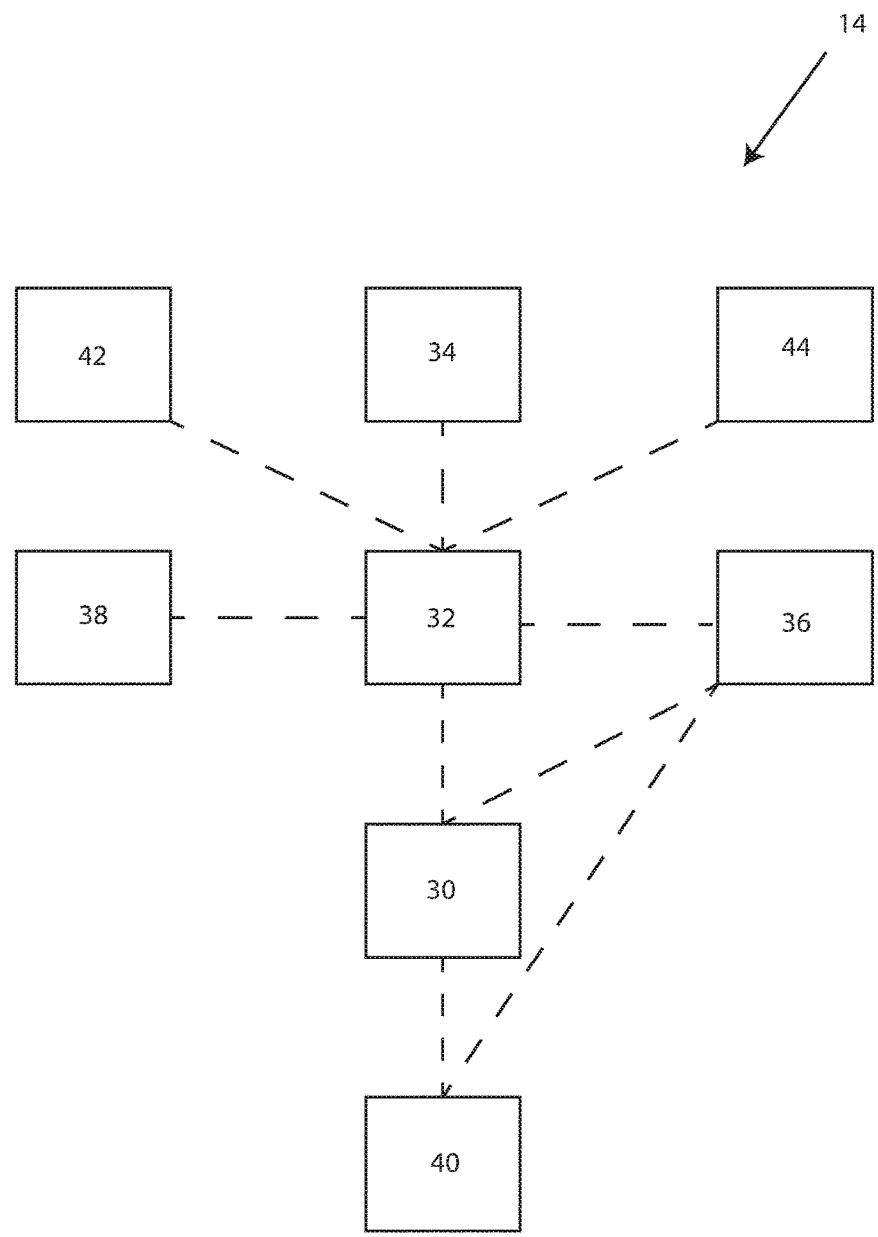
FIG. 4 of the drawings is schematic representation of an electronics assembly for use in accordance with the present invention.

Referring now to FIG. 4, electronics assembly 14 of sleep enhancement device 10 generally comprises energy source 30, circuit board/controller (e.g., printed circuit board) 32, primary user interface 34, light source 36, and speaker 38.

Energy source 30 is preferably at least partially contained within internal chamber 22 of containment assembly 12. Energy source 30 is also preferably in electrical communication with circuit board 32 and/or light source 36. Energy source 30 of the electronics assembly preferably comprises, for example, an AC power supply, a DC power supply, an AC-DC power supply, a primary electrochemical cell, a secondary electrochemical cell, and/or a fuel cell.

Circuit board/controller 32 is preferably at least partially contained within internal chamber 22 of containment assembly 12. Circuit board/controller 32 is preferably in electrical communication with energy source 30, primary user interface 34, light source 36, and speaker 38.

In a preferred embodiment of the present invention, circuit board/controller 32 of electronics assembly 14 comprises one or more components, such as a battery, a bridge rectifier, a capacitor, a central processing unit, a communications port, a control board, a crystal, a diode, a fuse, a graphics board, an inductor, an input port, an integrated circuit, a microprocessor, a memory module, an oscillator, an output port a potentiometer, a receiver, a relay, a resistor, a semiconductor, a transformer, a transistor, a tuner, a video processing unit, a wired communications hub, and/or a wireless communications hub.

Primary user interface 34 is preferably associated with at least one of the sidewalls, the top wall, and the bottom wall of the containment assembly. Primary user interface 34 is preferably in electrical communication with circuit board/controller 32. In one embodiment of the present invention, primary user interface 34 of electronics assembly 14 comprises a graphical user interface and/or a circuit board having a plurality of user interface buttons 26 (See FIG. 3).

Light source 36 of electronics assembly 14 is preferably at least partially contained within internal chamber 22 of containment assembly 12. Light source 36 is preferably in electrical communication with energy source 30 and/or circuit board/controller 32.

In accordance with the present invention, light source 36 of electronics assembly 14 preferably comprises a light-emitting diode, an organic light-emitting diode, a tri-color (RGB) light-emitting diode, an incandescent bulb, a tungsten-halogen bulb, a xenon bulb, a fluorescent bulb, a compact fluorescent lamp, a high-intensity discharge bulb and/or an electroconductive, lightable paint and/or material.

Speaker 38 of electronics assembly 14 is preferably at least partially contained within internal chamber 22 of containment assembly 12. Speaker 38 is preferably in electrical communication with circuit board/controller 32. Speaker 38 preferably comprises a mini-speaker and/or a micro-speaker.

As is best shown in FIGS. 3 and 4, electronics assembly 14 preferably comprises switch 40 that is associated with at least one of the sidewalls, the top wall, and the bottom wall of containment assembly 12. Switch 40 is preferably in electrical communication with energy source 30 and/or light source 36.

As is best shown in FIG. 4, electronics assembly 14 also preferably comprises microphone 42 that is in electrical communication with the circuit board/controller 30.

In one embodiment of the present invention, containment assembly 12 further comprises a reservoir for containing a scented product, and electronics assembly 14 further comprises fan 44. Fan 44 is preferably in electrical communication with printed circuit board/controller 32. Fan 44 is adapted to displace the scented product away from sleep enhancement device 10 and into the room of a user.

In another embodiment of the present invention, electronics assembly 14 further comprises one or more of a secondary energy source, a secondary light source, a secondary user interface, a secondary circuit board, a secondary speaker, a vibration mechanism, a white noise generator, a thermo sensor, a tactile sensor, and/or a display—all of which are preferably in electrical communication with circuit board/controller 32. Preferably, the display is adapted to display at least one of alpha-numeric content, temperature, time, image and/or graphic.

In a preferred embodiment of the present invention, electronics assembly 14 further comprises an image sensor that is in electrical communication with the circuit board. The image sensor preferably provides a user with an image (e.g., a photo, a video) associated with the area proximate sleep enhance device 10. Examples of suitable image sensors include video camera tubes, semiconductor charge-coupled devices (CCD), active pixel sensor in complementary metal-oxide-semiconductors (CMOS), N-type metal-oxide-semiconductors (NMOS, Live MOS), and back-side illuminated complementary metal-oxide-semiconductors (BSI-CMOS).

It will be understood that the above-identified image sensors are commercially available from a plurality of sources, including Agilent, Aptina, Canesta, Canon, Caeleste, CMOSIS, Dalsa, Eastman Kodak, ESS Technology, Fujifilm, MagnaChip, Matsushita, MAZeT GmbH, Mitsubishi, Nikon OmniVision Technologies, ON Semiconductor, Cypress Semiconductor, PixArt Imaging, Pixim, Samsung, Sharp, Sony, STMicroelectronics, Toshiba, TowerJazz, Town Line Technologies, TransChip, Trusight and Trusense Imaging—just to name a few suppliers.

Additional examples of suitable image sensors for use in accordance with the present invention include U.S. Pat. No. 6,359,323 B1 entitled "Color image sensor and method for fabricating the same," United States Patent Application Publication No. 2006/0043261 A1 entitled "Solid state image pickup device and image pickup system comprising it," U.S. Pat. No. 7,129,979 B1 entitled "Image sensor pixel for global electronic shuttering," United States Patent Application Publication No. 2004/0147059 A1 entitled "Method for manufacturing CMOS image sensor having microlens therein with high photosensitivity," U.S. Pat. No. 5,990,506 A entitled "Active pixel sensors with substantially planarized color filtering elements," U.S. Pat. No. 6,235,549 B1 entitled "Method and apparatus for employing a light shield to modulate pixel color responsivity," U.S. Pat. No. 6,765,276 B2 entitled "Bottom antireflection coating color filter process for fabricating solid state image sensors," U.S. Pat. No. 6,486,913 B1 entitled "Pixel array with shared reset circuitry," U.S. Pat. No. 6,872,584 B2 entitled "Solid state image sensor and method for fabricating the same," United States Patent Application Publication No. 2006/0011813 A1 entitled "Image sensor having a passivation layer exposing at least a main pixel array region and methods of fabricating the same," United States Patent Application Publication No. 2007/0187793 A1 entitled "Filter, color filter array, method of manufacturing the color filter array, and image sensor," U.S. Pat. No. 6,379,992 B2 entitled "Method for fabricating an image sensor," United States Patent Application Publication No. 2006/0138500 A1 entitled "CMOS image sensor and method for fabricating the same," United States Patent Application Publication No. 2005/0263839 A1 entitled "Photoelectric converting film stack type solid-state image pickup device, and method of producing the same," United States Patent Application Publication No. 2007/0090274 A1 entitled "Image sensors including active pixel sensor arrays," United States Patent Application Publication No. 2006/0157761 A1 entitled "Image sensor with self-boosting and methods of operating and fabricating the same," U.S. Pat. No. 6,369,417 B1 entitled "CMOS image sensor and method for fabricating the same," U.S. Pat. No. 6,127,668 A entitled "Solid state image pickup device and method for manufacturing the same," United States Patent Application Publication No. 2007/0023802 A1 entitled "CMOS image sensor and method of fabricating the same," United States Patent Application Publication No. 2005/0090035 A1 entitled "Method for fabricating CMOS image sensor protecting low temperature oxide delamination," and United States Patent Application Publication No. 2006/0261342 A1 entitled "Imaging device having a pixel cell with a transparent conductive interconnect line and the method of making the pixel cell"—all of which are hereby incorporated herein by reference in their entirety, including all references cited therein.

In operation, power button or switch 40 is used to turn the device on. At power up, a sound is preferably produced to alert the user that the unit is on and a light source illuminates. The light source coupled with a button or other activator is used as a quick catch so if the user feels like there is a monster near or if they wake up from a bad dream, then they can press this button and the device will make a sound like it is capturing something and report "All Clear" (or a similar system status message). If the user pushes any of interface buttons 26, which may optionally be backlit, then various noises will be played back. One could be for a trash can being emptied sound that simulates removal of any "captured and destroyed" bad dreams or imaginary monsters. Another button could play a soothing sound or audio file. Yet another button could play a user-recorded message or sound—perhaps from a parent to let the child know they love them. Using "mood color" interface button 28, the user can change the color of an internal light source (e.g., LED) which provides a glow effect through apertures 24 and/or openings (e.g., arches) associated with the device. There may also preferably be an audio/MP3 input jack on the front sidewall.

Sleep enhancement device 10 may also include a brightness control button on the side of the device that is used to increase and/or decrease the brightness of the internal light source (e.g., LED). A switch may also be located on the side of the device which allows the user to turn internal glow light source (e.g., LED) on or off. A sidewall or panel of the device, preferably the rear panel, preferably includes a compartment for accommodating two filters. Inside the device an optional fan can be utilized to blow air across or through a filter, on the output side of the fan, which may have essential oils (or other scented product) applied to it. This provides a soothing scent to the room in which the device is used and can be therapeutic to the user. The other filter is preferably on the input side of the fan and can be used to catch dust that may accumulate on the fan blades. This second filter can also be used as a means to show a child that the unit is actually "catching" bad dreams or monsters as the dust that will be caught in the filter could be described as such. A power jack to use A/C power adapter is also preferably located on the back panel. A battery pack may be located on the bottom wall, among other walls, of the device to power the device. Inside the device is preferably a control board, an LED board for the internal RGB LED (or other means of color light creation), a speaker to provide the sound feedback, and a microphone for the user to record with.

In another embodiment of the present invention, the device may incorporate, for example, a camera, 2-way communications, wireless connectivity, mobile phone or internet application interface, am/fm/satellite radio modules, LCD screen with or without capacitive or resistive touch interface, microSD memory card slot, USB interface, alarm clock function, headphone jack, heat/temperature sensor for possible fire detection or temperature display, smoke sensor for possible fire detection, gunshot sensor, haptic feedback sensor for user interface (i.e., notification of emptying of "trash container" or notifications), accelerometer or other device to detect vibration or shake (quality assurance as well as possible use for earthquake detection in states like California or countries like those in the Asia Pacific). Also, a container that can be removed and such that sprinkles, glitter or the like can be put in it manually or by a timing device to simulate that monsters or such were caught and disposed of.

In accordance with the present invention, sleep enhancement device 10 may optionally comprise one or more adjunct components and/or accessories, including, but not limited to, a child's toy, a wand, a remote control, a remote interactive component, an LCD display, means of projecting one or more images, etcetera.

The foregoing description merely explains and illustrates the invention and the invention is not limited thereto except insofar as the appended claims are so limited, as those skilled in the art who have the disclosure before them will be able to make modifications without departing from the scope of the invention.

What is claimed and desired to be secured by Letters Patent of the United States is:

1. A sleep enhancement device for toddlers and young children, consisting of:
   a containment assembly, wherein the containment assembly consists of:
      a front wall having an inner surface and an outer surface, wherein the front wall includes an aperture,
      a back wall having an inner surface and an outer surface,
      a left sidewall having an inner surface and an outer surface,
      a right sidewall having an inner surface and an outer surface,
      a top wall having an inner surface and an outer surface,
      a bottom wall having an inner surface and an outer surface, and
      wherein the front wall, the back wall, the left sidewall, the right sidewall, the top wall, and the bottom wall are in a spaced-apart relationship to define an internal chamber therebetween; and
   an electronics assembly, wherein the electronics assembly consists of an energy source, a light source, a primary user interface, a circuit board, and a speaker,
      wherein the energy source is contained within the internal chamber of the containment assembly, and wherein the energy source is in electrical communication with the circuit board and the light source,
      wherein the circuit board is contained within the internal chamber of the containment assembly, and wherein the circuit board is in electrical communication with the energy source, the light source, the primary user interface, and the speaker,
      wherein the primary user interface is positioned on the outer surface of the front wall, and wherein the primary user interface is in electrical communication with the circuit board,
      wherein the light source is contained within the internal chamber of the containment assembly, and wherein the light source is in electrical communication with the energy source and the circuit board, and
      wherein the speaker is contained within the internal chamber of the containment assembly, and wherein the speaker is in electrical communication with the circuit board.

* * * * *